United States Patent
Brannan

(10) Patent No.: US 10,390,882 B2
(45) Date of Patent: *Aug. 27, 2019

(54) FLOW RATE MONITOR FOR FLUID COOLED MICROWAVE ABLATION PROBE

(71) Applicant: COVIDIEN LP, Mansfield, MA (US)

(72) Inventor: Joseph D. Brannan, Lyons, CO (US)

(73) Assignee: Covidien LP, Mansfield, MA (US)

( * ) Notice: Subject to any disclaimer, the term of this patent is extended or adjusted under 35 U.S.C. 154(b) by 746 days.

This patent is subject to a terminal disclaimer.

(21) Appl. No.: 14/995,273

(22) Filed: Jan. 14, 2016

(65) Prior Publication Data

US 2016/0128774 A1    May 12, 2016

Related U.S. Application Data

(60) Continuation of application No. 14/066,099, filed on Oct. 29, 2013, now Pat. No. 9,237,927, which is a
(Continued)

(51) Int. Cl.
*A61B 18/12* (2006.01)
*A61B 18/18* (2006.01)
(Continued)

(52) U.S. Cl.
CPC .......... *A61B 18/1815* (2013.01); *A61B 18/18* (2013.01); *A61B 90/06* (2016.02);
(Continued)

(58) Field of Classification Search
CPC ................ A61B 18/18; A61B 18/1815; A61B 2018/1823; A61B 2018/1861;
(Continued)

(56) References Cited

U.S. PATENT DOCUMENTS 5,019,678 A * 5/1991 Templeton ........... H01H 35/405
200/81.9 M
5,231,997 A * 8/1993 Kikuchi ................. A61N 5/02
219/695
(Continued)

FOREIGN PATENT DOCUMENTS

DE        390937 C    3/1924
DE      1099658 B    2/1961
(Continued)

OTHER PUBLICATIONS

International Search Report PCT/US01/11218 dated Aug. 14, 2001.
(Continued)

*Primary Examiner* — Thomas A Giuliani
(74) *Attorney, Agent, or Firm* — Carter, DeLuca & Farrell LLP

(57) ABSTRACT

A microwave ablation system includes an antenna assembly configured to deliver microwave energy from a power source to tissue and a coolant source operably coupled to the power source and configured to selectively provide fluid to the antenna assembly via a fluid path. The system also includes a controller operably coupled to the power source and a sensor operably coupled to the fluid path and the controller. The sensor is configured to detect fluid flow through the fluid path and the controller is configured to control the energy source based on the detected fluid flow.

7 Claims, 5 Drawing Sheets

Related U.S. Application Data division of application No. 12/569,171, filed on Sep. 29, 2009, now Pat. No. 8,568,398.

(51) Int. Cl.
*A61B 90/00* (2016.01)
*A61B 18/00* (2006.01)

(52) U.S. Cl.
CPC ........... *A61B 2018/00017* (2013.01); *A61B 2018/00023* (2013.01); *A61B 2018/0094* (2013.01); *A61B 2018/00136* (2013.01); *A61B 2018/00178* (2013.01); *A61B 2018/00577* (2013.01); *A61B 2018/00636* (2013.01); *A61B 2018/00642* (2013.01); *A61B 2018/00684* (2013.01); *A61B 2018/00702* (2013.01); *A61B 2018/00744* (2013.01); *A61B 2018/00863* (2013.01); *A61B 2018/00988* (2013.01); *A61B 2018/1823* (2013.01); *A61B 2018/1838* (2013.01); *A61B 2018/1853* (2013.01); *A61B 2018/1869* (2013.01); *A61B 2090/062* (2016.02); *A61B 2090/064* (2016.02)

(58) Field of Classification Search
CPC .. A61B 2018/1869; A61B 2018/00863; A61B 2018/00636; A61B 2018/00642; A61B 2018/00666; A61B 2018/00618; A61B 2018/00672; A61B 2018/00702; A61B 2018/00708; A61B 2018/1853; A61B 2018/00023; A61B 2018/1838
USPC ........ 606/33, 34, 38, 42; 607/101, 104, 105, 607/113, 116, 154, 156
See application file for complete search history.

(56) References Cited

U.S. PATENT DOCUMENTS

| | | | |
|---|---|---|---|
| 5,445,622 A | 8/1995 | Brown | |
| 5,672,174 A | 9/1997 | Gough et al. | |
| 5,829,519 A | 11/1998 | Uthe | |
| 5,863,290 A | 1/1999 | Gough et al. | |
| 5,951,547 A | 9/1999 | Gough et al. | |
| 6,007,571 A | 12/1999 | Neilson et al. | |
| 6,273,886 B1 | 8/2001 | Edwards et al. | |
| 6,350,276 B1 | 2/2002 | Knowlton | |
| 6,358,245 B1 | 3/2002 | Edwards et al. | |
| 6,413,255 B1 | 7/2002 | Stern | |
| 6,440,158 B1 | 8/2002 | Saab | |
| 6,622,731 B2 | 9/2003 | Daniel et al. | |
| 6,666,862 B2 | 12/2003 | Jain et al. | |
| 6,673,070 B2 | 1/2004 | Edwards et al. | |
| 6,955,675 B2 | 10/2005 | Jain | |
| 7,108,696 B2 | 9/2006 | Daniel et al. | |
| 7,122,031 B2 | 10/2006 | Edwards et al. | |
| 7,160,296 B2 | 1/2007 | Pearson et al. | |
| 7,278,991 B2 | 10/2007 | Morris et al. | |
| 7,311,703 B2 | 12/2007 | Turovskiy et al. | |
| 7,344,533 B2 | 3/2008 | Pearson et al. | |
| 7,585,296 B2 | 9/2009 | Edwards et al. | |
| 7,625,371 B2 | 12/2009 | Morris et al. | |
| 7,749,011 B2 | 7/2010 | Arts et al. | |
| 7,863,984 B1 | 1/2011 | Behnke | |
| 7,875,024 B2 | 1/2011 | Turovskiy et al. | |
| 8,035,570 B2 | 10/2011 | Prakash et al. | |
| 8,038,693 B2 | 10/2011 | Allen | |
| 8,059,059 B2 | 11/2011 | Bonn | |
| 8,118,808 B2 | 2/2012 | Smith et al. | |
| 8,181,649 B2 | 5/2012 | Brunner | |
| 8,182,480 B2 | 5/2012 | Huseman | |
| 8,192,427 B2 | 6/2012 | Buysse | |
| 8,197,473 B2 | 6/2012 | Rossetto et al. | |
| 8,202,270 B2 | 6/2012 | Rossetto et al. | |
| 8,211,098 B2 | 7/2012 | Paulus | |
| 8,216,227 B2 | 7/2012 | Podhajsky | |
| 8,221,418 B2 | 7/2012 | Prakash et al. | |
| 8,235,981 B2 | 8/2012 | Prakash et al. | |
| 8,251,987 B2 | 8/2012 | Willyard | |
| 8,282,632 B2 | 10/2012 | Rossetto | |
| 8,292,881 B2 | 10/2012 | Brannan et al. | |
| 8,328,799 B2 | 12/2012 | Brannan | |
| 8,328,800 B2 | 12/2012 | Brannan | |
| 8,328,801 B2 | 12/2012 | Brannan | |
| 8,334,812 B2 | 12/2012 | Brannan | |
| 8,343,145 B2 | 1/2013 | Brannan | |
| 8,343,149 B2 | 1/2013 | Rossetto et al. | |
| 8,353,903 B2 | 1/2013 | Podhajsky | |
| 8,355,803 B2 | 1/2013 | Bonn et al. | |
| 8,382,750 B2 | 2/2013 | Brannan | |
| 8,394,086 B2 | 3/2013 | Behnke et al. | |
| 8,394,087 B2 | 3/2013 | Willyard et al. | |
| 8,394,092 B2 | 3/2013 | Brannan | |
| 8,409,187 B2 | 4/2013 | Bonn | |
| 8,430,871 B2 | 4/2013 | Brannan | |
| 8,463,396 B2 | 6/2013 | Podhajsky | |
| 8,512,328 B2 | 8/2013 | Rossetto et al. | |
| 8,545,493 B2 | 10/2013 | Brannan et al. | |
| 8,552,915 B2 | 10/2013 | Brannan | |
| 8,556,889 B2 * | 10/2013 | Brannan ................ | A61B 18/18 606/33 |
| 8,568,398 B2 * | 10/2013 | Brannan ................ | A61B 18/18 606/33 |
| 8,568,401 B2 | 10/2013 | Brannan | |
| 8,834,409 B2 | 9/2014 | Manley | |
| 8,834,460 B2 | 9/2014 | Peterson | |
| 8,876,814 B2 | 11/2014 | Bonn | |
| 8,906,007 B2 | 12/2014 | Bonn et al. | |
| 8,945,114 B2 | 2/2015 | Elmouelhi et al. | |
| 9,024,237 B2 | 5/2015 | Bonn | |
| 9,031,668 B2 | 5/2015 | DeCarlo | |
| 9,095,359 B2 | 8/2015 | Behnke, II et al. | |
| 9,113,624 B2 | 8/2015 | Belous et al. | |
| 9,113,924 B2 | 8/2015 | Brannan et al. | |
| 9,113,925 B2 | 8/2015 | Smith et al. | |
| 9,113,926 B2 | 8/2015 | Brannan et al. | |
| 9,173,706 B2 | 11/2015 | Rossetto | |
| 9,192,436 B2 | 11/2015 | Willyard et al. | |
| 9,237,927 B2 | 1/2016 | Brannan | |
| 9,271,796 B2 | 3/2016 | Buysse et al. | |
| 9,277,969 B2 | 3/2016 | Brannan et al. | |
| 2004/0082903 A1* | 4/2004 | Micheli ................ | A61M 1/1696 604/29 |
| 2005/0113893 A1 | 5/2005 | Saab | |
| 2007/0203551 A1 | 8/2007 | Cronin et al. | |
| 2009/0299364 A1 | 12/2009 | Batchelor et al. | |
| 2010/0030206 A1 | 2/2010 | Brannan et al. | |
| 2010/0030210 A1 | 2/2010 | Paulus | |
| 2010/0045559 A1 | 2/2010 | Rossetto | |
| 2010/0076422 A1 | 3/2010 | Podhajsky | |
| 2010/0087808 A1 | 4/2010 | Paulus | |
| 2010/0094273 A1 | 4/2010 | Rossetto et al. | |
| 2010/0262134 A1 | 10/2010 | Jensen et al. | |
| 2010/0331834 A1 | 12/2010 | Peterson et al. | |
| 2011/0054458 A1 | 3/2011 | Behnke | |
| 2011/0054459 A1 | 3/2011 | Peterson | |
| 2011/0071511 A1 | 3/2011 | Brannan et al. | |
| 2011/0118723 A1* | 5/2011 | Turner ................ | A61B 18/1815 606/33 |
| 2011/0118731 A1 | 5/2011 | Ladtkow | |

FOREIGN PATENT DOCUMENTS

| | | | |
|---|---|---|---|
| DE | 1139927 B | 11/1962 | |
| DE | 1149832 B | 6/1963 | |
| DE | 1439302 A1 | 1/1969 | |
| DE | 2439587 A1 | 2/1975 | |
| DE | 2455174 A1 | 5/1975 | |
| DE | 2407559 A1 | 8/1975 | |
| DE | 2415263 A1 | 10/1975 | |

(56) References Cited

FOREIGN PATENT DOCUMENTS

| | | |
|---|---|---|
| DE | 2429021 A1 | 1/1976 |
| DE | 2460481 A1 | 6/1976 |
| DE | 2602517 A1 | 7/1976 |
| DE | 2504280 A1 | 8/1976 |
| DE | 2627679 A1 | 1/1977 |
| DE | 2540968 A1 | 3/1977 |
| DE | 2820908 A1 | 11/1978 |
| DE | 2803275 A1 | 8/1979 |
| DE | 2823291 A1 | 11/1979 |
| DE | 2946728 A1 | 5/1981 |
| DE | 3143421 A1 | 5/1982 |
| DE | 3045996 A1 | 7/1982 |
| DE | 3120102 A1 | 12/1982 |
| DE | 3510586 A1 | 10/1986 |
| DE | 3604823 A1 | 8/1987 |
| DE | 8712328 U1 | 2/1988 |
| DE | 3711511 C1 | 6/1988 |
| DE | 3904558 A1 | 8/1990 |
| DE | 3942998 A1 | 7/1991 |
| DE | 4238263 A1 | 5/1993 |
| DE | 04303882 C2 | 2/1995 |
| DE | 4339049 A1 | 5/1995 |
| DE | 29616210 U1 | 11/1996 |
| DE | 19608716 C1 | 4/1997 |
| DE | 19751106 A1 | 5/1998 |
| DE | 19717411 A1 | 11/1998 |
| DE | 19751108 A1 | 5/1999 |
| DE | 19801173 C1 | 7/1999 |
| DE | 19848540 A1 | 5/2000 |
| DE | 10224154 A1 | 12/2003 |
| DE | 10328514 B3 | 3/2005 |
| DE | 102004022206 A1 | 12/2005 |
| DE | 202005015147 U1 | 2/2006 |
| EP | 0 246 350 A1 | 11/1987 |
| EP | 0 521 264 A2 | 1/1993 |
| EP | 0 556 705 A1 | 8/1993 |
| EP | 0 558 429 A1 | 9/1993 |
| EP | 0 836 868 A2 | 4/1998 |
| EP | 1159926 A3 | 3/2003 |
| FR | 179 607 | 11/1906 |
| FR | 1 275 415 A | 11/1961 |
| FR | 1 347 865 A | 1/1964 |
| FR | 2 235 669 A1 | 1/1975 |
| FR | 2 276 027 A1 | 1/1976 |
| FR | 2 313 708 A1 | 12/1976 |
| FR | 2 502 935 A1 | 10/1982 |
| FR | 2 517 953 A1 | 6/1983 |
| FR | 2 573 301 A1 | 5/1986 |
| FR | 2 862 813 A1 | 5/2005 |
| FR | 2 864 439 A1 | 7/2005 |
| JP | 5-5106 | 1/1993 |
| JP | 05-40112 | 2/1993 |
| JP | 06343644 A | 12/1994 |
| JP | 07265328 A | 10/1995 |
| JP | 08056955 | 3/1996 |
| JP | 08252263 A | 10/1996 |
| JP | 09010223 | 1/1997 |
| JP | 11244298 A | 9/1999 |
| JP | 2000342599 A | 12/2000 |
| JP | 2000350732 A | 12/2000 |
| JP | 2001008944 A | 1/2001 |
| JP | 2001029356 A | 2/2001 |
| JP | 2001128990 A | 5/2001 |
| SU | 166452 | 1/1965 |
| SU | 401367 A1 | 10/1973 |
| SU | 727201 A1 | 4/1980 |
| WO | 97/06739 A2 | 2/1997 |
| WO | 97/06740 A2 | 2/1997 |
| WO | 97/06855 A2 | 2/1997 |
| WO | 9944520 A1 | 9/1999 |
| WO | 0044520 A1 | 8/2000 |
| WO | 00/53113 A1 | 9/2000 |
| WO | 2005/011049 A2 | 2/2005 |

OTHER PUBLICATIONS

International Search Report PCT/US01/11224 dated Nov. 13, 2001.
International Search Report PCT/US01/11340 dated Aug. 16, 2001.
International Search Report PCT/US01/11420 dated Oct. 16, 2001.
International Search Report PCT/US02/01890 dated Jul. 25, 2002.
International Search Report PCT/US02/11100 dated Jul. 16, 2002.
International Search Report PCT/US03/09483 dated Aug. 13, 2003.
International Search Report PCT/US03/22900 dated Dec. 2, 2003.
International Search Report PCT/US03/37110 dated Jul. 25, 2005.
International Search Report PCT/US03/37111 dated Jul. 28, 2004.
International Search Report PCT/US03/37310 dated Aug. 13, 2004.
International Search Report PCT/US04/04685 dated Aug. 27, 2004.
International Search Report PCT/US04/13273 dated Dec. 15, 2004.
International Search Report PC/US04/15311 dated Jan. 12, 2004.
International Search Report PCT/US05/36168 dated Aug. 28, 2006.
International Search Report PCT/US08/052460 dated Apr. 24, 2008.
International Search Report PCT/US09/31658 dated Mar. 11, 2009.
US. Appl. No. 08/483,742, filed Jun. 7, 1995.
U.S. Appl. No. 08/136,098, filed Oct. 14, 1993.
Anderson et al., "A Numerical Study of Rapid Heating for High Temperature Radio Frequency Hyperthermia" International Journal of Bio-Medical Computing, 35 (1994), pp. 297-307.
Anonymous. (2001) Disposable Chiba Biopsy Needles and Trays, Biopsy and Special Purpose Needles Cook Diagnostic and Interventional Products Catalog (products list), 4 pages.
Carbonell et al., "Comparison of the Gyrus PlasmaKinetic Sealer and the Valleylab LigaSure.TM. Device in the Hemostasis of Small, Medium, and Large-Sized Arteries" Carolinas Laparoscopic and Advanced Surgery Program, Carolinas Medical Center,Charlotte, NC 2003.
Bosman et al., "Methods of Making Nervous System Lesions" in William RH, Rengachary SS (eds): Neurosurgery, New York: McGraw.cndot.Hill, vol. 111, (1984), pp. 2490-2499.
Goldberg et al., "Image-guided Radiofrequency Tumor Ablation: Challenges and Opportunities—Part I", (2001) J Vasc. Interv. Radiol., vol. 12, pp. 1021-1032.
Herman at al., "Laparoscopic Intestinal Resection With the LigaSure.TM. Vessel Sealing System: A Case Report" Innovations That Work, Feb. 2002.
Humphries Jr. et al., "Finite.cndot.Element Codes to Model Electrical Heating and Non.cndot.LInear Thermal Transport in Biological Media", Proc. ASME HTD-355, 131 (1997).
Johnson, "Evaluation of the LigaSure.TM. Vessel Sealing System in Hemorrhoidectormy" American College of Surgeons (ACS) Clinic La Congress Poster (2000).
Kennedy et al., "High-burst-strength, feedback-controlled bipolar vessel sealing" Surgical Endoscopy (1998) 12: 876-878.
Koyle et al., "Laparoscopic Palomo Varicocele Ligation in Children and Adolescents" Pediatric Endosurgery & Innovative Techniques, vol. 6, No. 1, 2002.
Lyndon B. Johnson Space Center, Houston, Texas, "Compact Directional Microwave Antenna for Localized Heating," NASA Tech Briefs, Mar. 2008.
M. A. Astrahan, "A Localized Current Field Hyperthermia System for Use with 192-Iridium Interstitial Implants" Medical Physics. 9(3), May/Jun. 1982.
Michael Choti, "Abdominoperineal Resection with the LigaSure.TM. Vessel Sealing System and LigaSure.TM. Atlas 20 cm Open Instrument" Innovations That Work, Jun. 2003.
Ni Wei et al., "A Signal Processing Method for the Coriolis Mass Flowmeter Based on a Normalized . . . " Journal of Applied Sciences.cndot.Yingyong Kexue Xuebao, Shangha CN, vol. 23, No. 2:(Mar. 2005); pp. 160-184.
Peterson et al., "Comparison of Healing Process Following Ligation with Sutures and Bipolar Vessel Sealing" Surgical Technology International (2001).
T. Seki et al., (1994) "Ultrasonically Guided Percutaneous Microwave Coagulation Therapy for Small Hepatocellular carcinoma," Cancer 74(3):817.cndot.825.
Wald et al., "Accidental Burns", JAMA, Aug. 16, 1971, vol. 217, No. 7, pp. 916-921.

(56) References Cited

OTHER PUBLICATIONS

Walt Boyles, "Instrumentation Reference Book", 2002, Butterworth-Heinemann, pp. 262-264.
European Search Report EP 07007783.9 dated Aug. 14, 2007.
International Search Report PCT/US98/18640 dated Jan. 29, 1998.
Urologix, Inc.—Medical Professionals: Targis.TM. Technology (Date Unknown). "Overcoming the Challenge" located at: <http://www.urologix.com!medicaUtechnology.html > Nov. 18, 1999; 3 pages.
Alexander et al., "Magnetic Resonance Image-Directed Stereotactic Neurosurgery: Use of Image Fusion with computerized Tomography to Enhance SpatialAccuracy" Journal Neurosurgery, 83 (1995), pp. 271-276.
Anderson et al., "A Numerical Study of Rapid Heating for High Temperature Radio Frequency Hyperthermia" International Journal of Bio-Medicai Computing, 35 (1994), pp. 297-307.
Anonymous. (1999) Auto Suture MIBB Site Marker: Single Use Clip Applier, United States Surgical (Product Instructions), 2 pages.
Anonymous. (2001) Disposable Chiba Biopsy Needles and Tray, Biopsy and Special Purpose Needles Cook Diagnostic and Interventional Products Catalog (products list), 4 pages.
Anonymous. (1987) Homer Mammalok.TM. Breast Lesion Needle/Wire Localizer, Namic.RTM. Angiographic Systems Division, Glens Falls, New York, (Hospital products price list), 4 pages.
Anonymous, (1999) MIBB Site Marker, United States Surgical (Sales brochure), 4 pages.
Anonymous, Blunt Tubes with Finished Ends. Pointed Cannula, Popper & Sons Biomedical Instrument Division, (Products Price List), one page; Jul. 19, 2000.
Anonymous. Ground Cannulae, ISPG, New Milford, CT; (Advertisement) one page, Jul. 19, 2000.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Durney et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure.TM. Device in the Hemostatsis of Small, Medium, and Large-Sized Arteries" Carolinas Laparoscopic and Advanced Surgery Program, Carolinas Medical Center,Charlotte, NC 2003.
Carus et al., "Initial Experience With the LigaSure.TM. Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 941n Biologic Effects of Nonionizing Electromagnetic Fields, CRC Press, Inc., pp. 1424-1428.
Chung et al., "Clinical Experience of Sutureless Closed Hemorrhoidectomy with LigaSure.TM." Diseases of the Colon & Rectum, vol. 46, No. 1, Jan. 2003.

Cosman et al., "Methods of Making Nervous System Lesions" In William R.H, Rengachary SS (eds); Neurosurgery, New York; McGraw Hill, vol. 111, (1984), pp. 2490-2499.
Cosman et al., "Radiofrequency Lesion Generation and its Effect on Tissue Impedance", Applied Neurophysiology, 51:230-242, 1988.
Cosman et al., "Theoretical Aspects of Radiofrequency Lesions in the Dorsal Root Entry Zone" Neurosurgery 15: (1984), pp. 945-950.
Crawford et al., "Use of the LigaSure.TM. Vessel Sealing System in Urologic Cancer Surger" Grand Rounds in Urology 1999, vol. 1, Issue 4, pp. 10-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David. Crawford, "Use of a Novel Vessel Sealing Technology in Management of the Dorsal Veinous Complex" Sales/Product Literature 2000.
Esterline Product Literature, "Light Key: Visualize a Virtual Keyboard. One With No Moving Parts", Nov. 1, 2003; 4 pages.
Geddes et al., "The Measurement of Physiologic Events by Electrical Impedance" Am. J. MI, Jan. Mar. 1964, pp. 16-27.
Goldberg et al "Image-guided Radiofrequency Tumor Ablation: Challenges and Opportunties—Part 1", (2001) J Vasc. Interv. Radiol, vol. 12, pp. 1021-1032.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.
Heniford et al., "Initial Results with an Electrothermal Bipolar Vessel Sealer" Surgical Endoscopy (2001) 15:799-801.
Herman at al., "Laparoscopic Intestinal Resection With LigaSure. TM. Vessel Sealing System: A Case Report" Innovations That Work, Feb. 2002.
Humphries Jr. et al., "Finite-Element Codes to Model Electrical Heating and Non-Linear Thermal Transport in Biological Media", Proc. ASME HTD-355, 131 (1997).
Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.
Jarrett et al., "Use of the LigaSure.TM. Vessel Sealing System for Peri-Hilar Vessels in Laparoscopic Nephrectomy" Sales/Product Literature 2000.
Johnson et al., "Evaluation of a Bipolar Electrothermal Vessel Sealing Device in Hemorrhoidectomy" Sales/Product Literature, Jan. 2004.
Johnson, "Evaluation of LigaSure.TM. Vessel Sealing System in Hemorrhoidectormy" American College of Surgeons (ACS) Clinic La Congress Poster (2000).
Johnson, "Use of the LigaSure.TM. Vessel Sealing System in Bloodless Hemorrhoidectomy" Innovations That Work, Mar. 2000.
Joseph G. Andriole M.D. et al., "Biopsy Needle Characteristics Assessed in the Laboratory", Radiology 148: 659-662, Sep. 1983.
Joseph Ortenberg, "LigaSure.TM. System Used in Laparoscopic 1st and 2nd Stage Orchiopexy" Innovations That Work, Nov. 2002.
K. Ogata, Modern Control Engineering, Prentice-Hall, Englewood Cliffs, N.J., 1970.
Kennedy et al., "High-burst-strenglh, feedback-controlled bipolar vessel sealing" Surgical Endoscopy (1998) 12: 876-878.
Kopans, D.B. et al., (Nov. 1985) "Spring Hookwire Breast Lesion Localizer: Use with Rigid-Compression, Mammographic Systems," Radiology 157(2):537-538.
Koyle et al., "Laparoscopic Palomo Varicocele Litigation in Children and Adolescents" Pediatric Endosurgery & Innovative Techniques, vol. 6, No. 1, 2002.
LigaSure.TM. Vessel Sealing System, the Seal of Confidence in General, Gynecologic, Urologic, and Laparaoscopic Surgery, Sales/Product Literature, Jan. 2004.

(56) References Cited

OTHER PUBLICATIONS

Livraghi et al., (1995) "Saline-enhanced RF Tissue Ablation in the Treatment of Liver Metastases", Radiology, pp. 205-210.
European Search Report EP 04027314 dated Mar. 31, 2005.
European Search Report EP 04027479 dated Mar. 17, 2005.
European Search Report EP 04027705 dated Feb. 10, 2005.
European Search Report EP 04710258 dated Oct. 15, 2004.
European Search Report EP 0475234.6 dated Jul. 31, 2007.
European Search Report EP 04778192.7 dated Jul. 1, 2009.
European Search Report EP 05002027.0 dated May 12, 2005.
European Search Report EP 05002769.7 dated Jun. 19, 2006.
European Search Report EP 05013463.4 dated Oct. 7, 2005.
European Search Report EP 05013895 dated Oct. 21, 2005.
European Search Report EP 05014156.3 dated Jan. 4, 2006.
European Search Report EP 05016399 dated Jan. 13, 2006.
European Search Report EP 05017281 dated Nov. 24, 2005.
European Search Report EP 05019130.3 dated Oct. 27, 2005.
European Search Report EP 05019882 dated Feb. 16, 2006.
European Search Report EP 05020665.5 dated Feb. 27, 2006.
European Search Report EP 05020666.3 dated Feb. 27, 2006.
European Search Report EP 05021025.1 dated Mar. 13, 2006.
European Search Report EP 05021197.8 dated Feb. 20, 2006.
European Search Report EP 05021777 dated Feb. 23, 2006.
European Search Report EP 05021779.3 dated Feb. 2, 2006.
European Search Report EP 05021780.1 dated Feb. 23, 2006.
European Search Report EP 05021935 dated Jan. 27, 2006.
European Search Report EP 05021936.9 dated Feb. 6, 2006.
European Search Report EP 05021937.7 dated Jan. 23, 2006.
European Search Report EP 05021939 dated Jan. 27, 2006.
European Search Report EP 05021944.3 dated Jan. 25, 2006.
European Search Report EP 05022350.2 dated Jan. 30, 2006.
European Search Report EP 05023017.6 dated Feb. 24, 2006.
European Search Report EP 05025423.4 dated Jan. 19, 2007.
European Search Report EP 05025424 dated Jan. 30, 2007.
European Search Report EP 05810523 dated Jan. 29, 2009.
European Search Report EP 06000708.5 dated May 15, 2006.
European Search Report EP 06002279.5 dated Mar. 30, 2006.
European Search Report EP 06005185.1 dated May 10, 2006.
European Search Report EP 06005540 dated Sep. 24, 2007.
European Search Report EP 06006717.0 dated Aug. 11, 2006.
European Search Report EP 06006961 dated Oct. 22, 2007.
European Search Report EP 06006963 dated Jul. 25, 2006.
European Search Report EP 06008779.8 dated Jul. 13, 2006.
European Search Report EP 06009435 dated Jul. 13, 2006.
European Search Report EP 06010499.9 dated Jan. 29, 2008.
European Search Report EP 06014461.5 dated Oct. 31, 2006.
European Search Report EP 06018206.0 dated Oct. 20, 2006.
European Search Report EP 06019768 dated Jan. 17, 2007.
European Search Report EP 06020574.7 dated Oct. 2, 2007.
European Search Report EP 06020583.8 dated Feb. 7, 2007.
European Search Report EP 06020584.6 dated Feb. 1, 2007.
European Search Report EP 06020756.0 dated Feb. 16, 2007.
European Search Report EP 06022028.2 dated Feb. 13, 2007.
European Search Report EP 06023756.7 dated Feb. 21, 2008.
European Search Report EP 06024122.1 dated Apr. 16, 2007.
European Search Report EP 06024123.9 dated Mar. 6, 2007.
European Search Report EP 06025700.3 dated Apr. 12, 2007.
European Search Report EP 07000885.9 dated May 15, 2007.
European Search Report EP 07001480.8 dated Apr. 19, 2007.
European Search Report EP 07001481.6 dated May 2, 2007.
European Search Report EP 07001485.7 dated May 23, 2007.
European Search Report EP 07001488.1 dated Jun. 5, 2007.
European Search Report EP 07001489.9 dated Dec. 20, 2007.
European Search Report EP 07001491 dated Jun. 6, 2007.
European Search Report EP 07001527.6 dated May 18, 2007.
European Search Report EP 07007783.9 dated Aug. 4, 2007.
European Search Report EP 07008207.8 dated Sep. 13, 2007.
European Search Report EP 07009026.1 dated Oct. 8, 2007.
European Search Report EP 07009028 dated Jul. 16, 2007.
European Search Report EP 07009029.5 dated Jul. 20, 2007.
European Search Report EP 07009321.6 dated Aug. 28, 2007.
European Search Report EP 07009322.4 dated Jan. 14, 2008.
European Search Report EP 07010672.9 dated Oct. 16, 2007.
European Search Report EP 07010673.7 dated Oct. 5, 2007.
European Search Report EP 07013779.9 dated Oct. 26, 2007.
European Search Report EP 07015191.5 dated Jan. 23, 2007.
European Search Report EP 07015601.3 dated Jan. 4, 2007.
European Search Report EP 07015602.1 dated Dec. 20, 2007.
European Search Report EP 07018375.1 dated Jan. 8, 2008.
European Search Report EP 07018821 dated Jan. 14, 2008.
European Search Report EP 07019173.9 dated Feb. 12, 2008.
European Search Report EP 07019174.7 dated Jan. 29, 2008.
European Search Report EP 07019178.8 dated Feb. 12, 2008.
European Search Report EP 07020283.3 dated Feb. 5, 2008.
European Search Report EP 07253835.8 dated Dec. 20, 2007.
European Search Report EP 08001019 dated Sep. 23, 2008.
European Search Report EP 08004975 dated Jul. 24, 2008.
European Search Report EP 08006731.7 dated Jul. 29, 2008.
European Search Report EP 08006733 dated Jul. 7, 2008.
European Search Report EP 08006734.1 dated Aug. 18, 2008.
European Search Report EP 08006735.8 dated Jan. 8, 2009.
European Search Report EP 08011282 dated Aug. 14, 2009.
European Search Report EP 08011705 dated Aug. 20, 2009.
European Search Report EP 08012829.1 dated Oct. 29, 2008.
European Search Report EP 08015842 dated Dec. 5, 2008.
European Search Report EP 08019920.1 dated Mar. 27, 2009.
European Search Report EP 08169973.8 dated Apr. 6, 2009.
European Search Report EP 09156861.8 dated Aug. 4, 2009.
European Search Report EP 09161502.1 dated Sep. 2, 2009.
European Search Report EP 09166708 dated Oct. 15, 2009.
International Search Report PCT/U598/18640 dated Jan. 29, 1998.
International Search Report PCT/US98/23950 dated Jan. 14, 1998.
International Search Report PCT/US99/24869 dated Feb. 11, 2000.
Lyndon B. Johnson Space Center, Houston, Texas, "Compact Direcetional Microwave Antenna for Localized Heating," NASA Tech Briefs, Mar. 2008.
M. A. Astrahan, "A Localized Curient Field Hyperthermia System for Use with 192-Iridium Interstitial Implants" Medical Physics. 9(3), May/Jun. 1982.
Magdy F. Iskander et al., "Design Optimization of Interstitial Antennas", IEEE Transactions on Biomedical Engineering, vol. 36, No. 2, Feb. 1989, pp. 238-246.
McGahan et al., (1995) "Percutaneous Ultrasound-guided Radiofrequency Electrocautery Ablation of Prostate Tissue in Dogs", Acad Radiol, vol. 2, No. 1, pp. 61-65.
McLellan et al., "Vessel Sealing for Hemostasis During Pelvic Surgery" Int'l Federation of Gynecology and Obstetrics FIGO World Congress 2000, Washington, DC.
MDTECH product literature (Dec. 1999) "FlexStrand"; product description, 1 page.
MDTECH product literature (Mar. 2000) I'D Wire: product description, 1 page.
Medtrex Brochure "The O.R. Pro 300" 1 page, Sep. 1998.
Michael Choti, "Abdominoperineal Resection with LigaSure.TM. Vessel Sealing System and LigaSure.TM. Atlas 20 cm Open Instrument" Innovations That Work, Jun. 2003.
Muller et al., "Extended Left Hemicolectomy Using the LigaSure. TM. Vessel Sealing System" Innovations That Work. LJ, Sep. 1999.
Murakami, R. et al., (1995), "Treatment of Hepatocellular Carcinoma: Value of Percutaneous Microwave Coagulation," American Journal of Radiology (AJR) 164:1159-1164.
Ni Wei el al., "A Signal Processing Method for the Coriolis Mass Flowmeter Based on a Normalized . . . " Journal of Applied Sciences Yingyong Kexue Xuebao, Shangha CN, vol. 23, No. 2:(Mar. 2005); pp. 160-184.
Ogden, "Goertzel Alternative to the Fourier Transform" Jun. 1993 pp. 485-487 Electronics World; Reed Business Publishing, Sutton, Surrey, BG, vol. 99, No. 9, 1687.
Olsson M.D. et al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol, vol. 39; pp. 69-76 (1976/77).

(56) References Cited

OTHER PUBLICATIONS

P.R. Stauffer et al., "Interstitial Heating Technologies", Thermoradiotheray and Thermochemotherapy (1995) vol. I, Biology, Physiology, Physics, pp. 279-320.
Palazzo et al. "Randomized clinical trial of LigaSure.TM. versus open haemorrhoidectomy" British Journal of Surgery 2002,89,154-157 "Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Apr. 2001, pp. 236-237.
Peterson et at., "Companion of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1 ):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSure.TM. Vessel Sealing System in Minimally Invasive Surgery in Children" Int'l Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001) 71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.
Stuart W. Young, Nuclear Magnetic Resonance Imaging—Basic Principles, Raven Press, New York, 1984.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817-825.
Urologix, Inc..about.Medical Professionals: Targis.TM. Technology (Date Unknown). "Overcoming the Challenge" located at: <http://www.urologix.comlmedicaUtechnology.html> Nov. 19, 1999; 3 pages.
Urrutia et al., (1988), "Retractable-Barb Needle for Breast Lesion Localization: Use in 60 Cases," Radiology 169 (3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation-'COA-COMP'" Neurosurgical Review 7:2-3(1984) pp. 187-190.
W. Scott Helton, "LigaSure.TM. Vessel Sealing System: Revolutionary Hemostasis Product for General Surgery" Sales/Product Literature 1999.
Wait Boyles, "Instrumentation Reference Book", 2002, Butterworth-Heinemann, pp. 262-264.
European Search Report EP 98300964.8 dated Dec. 13, 2000.
European Search Report EP 98944778 dated Nov. 7, 2000.
European Search Report EP 98958575.7 dated Oct. 29, 2002.
European Search Report EP 03721482 dated Feb. 6, 2006.
European Search Report EP 04009964 dated Jul. 28, 2004.
European Search Report EP 04013772 dated Apr. 11, 2005.
European Search Report EP 04015980 dated Nov. 3, 2004.
European Search Report EP 04015981.6 dated Oct. 25, 2004.

* cited by examiner

FLOW RATE MONITOR FOR FLUID COOLED MICROWAVE ABLATION PROBE

CROSS-REFERENCE TO RELATED APPLICATIONS

The present application is a continuation application of U.S. patent application Ser. No. 14/066,099, filed on Oct. 29, 2013, now U.S. Pat. No. 9,237,927, which is a divisional application of U.S. patent application Ser. No. 12/569,171, filed on Sep. 29, 2009, now U.S. Pat. No. 8,568,398, the entire contents of all of which are incorporated by reference herein.

BACKGROUND

1. Technical Field

The present disclosure relates generally to microwave ablation procedures that utilize microwave surgical devices having a microwave antenna that may be inserted directly into tissue for diagnosis and treatment of diseases. More particularly, the present disclosure is directed to a system and method for monitoring correct system operation of a microwave ablation system.

2. Background of Related Art

In the treatment of diseases such as cancer, certain types of cancer cells have been found to denature at elevated temperatures (which are slightly lower than temperatures normally injurious to healthy cells.) These types of treatments, known generally as hyperthermia therapy, typically utilize electromagnetic radiation to heat diseased cells to temperatures above 41° C., while maintaining adjacent healthy cells at lower temperatures where irreversible cell destruction will not occur. Other procedures utilizing electromagnetic radiation to heat tissue also include ablation and coagulation of the tissue. Such microwave ablation procedures, e.g., such as those performed for menorrhagia, are typically done to ablate and coagulate the targeted tissue to denature or kill the tissue. Many procedures and types of devices utilizing electromagnetic radiation therapy are known in the art. Such microwave therapy is typically used in the treatment of tissue and organs such as the prostate, heart, liver, lung, kidney, and breast.

One non-invasive procedure generally involves the treatment of tissue (e.g., a tumor) underlying the skin via the use of microwave energy. The microwave energy is able to non-invasively penetrate the skin to reach the underlying tissue. However, this non-invasive procedure may result in the unwanted heating of healthy tissue. Thus, the non-invasive use of microwave energy requires a great deal of control.

Presently, there are several types of microwave probes in use, e.g., monopole, dipole, and helical. One type is a monopole antenna probe, which consists of a single, elongated microwave conductor exposed at the end of the probe. The probe is typically surrounded by a dielectric sleeve. The second type of microwave probe commonly used is a dipole antenna, which consists of a coaxial construction having an inner conductor and an outer conductor with a dielectric junction separating a portion of the inner conductor. The inner conductor may be coupled to a portion corresponding to a first dipole radiating portion, and a portion of the outer conductor may be coupled to a second dipole radiating portion. The dipole radiating portions may be configured such that one radiating portion is located proximally of the dielectric junction, and the other portion is located distally of the dielectric junction. In the monopole and dipole antenna probe, microwave energy generally radiates perpendicularly from the axis of the conductor.

The typical microwave antenna has a long, thin inner conductor that extends along the axis of the probe and is surrounded by a dielectric material and is further surrounded by an outer conductor around the dielectric material such that the outer conductor also extends along the axis of the probe. In another variation of the probe that provides for effective outward radiation of energy or heating, a portion or portions of the outer conductor can be selectively removed. This type of construction is typically referred to as a "leaky waveguide" or "leaky coaxial" antenna. Another variation on the microwave probe involves having the tip formed in a uniform spiral pattern, such as a helix, to provide the necessary configuration for effective radiation. This variation can be used to direct energy in a particular direction, e.g., perpendicular to the axis, in a forward direction (i.e., towards the distal end of the antenna), or combinations thereof.

Invasive procedures and devices have been developed in which a microwave antenna probe may be either inserted directly into a point of treatment via a normal body orifice or percutaneously inserted. Such invasive procedures and devices potentially provide better temperature control of the tissue being treated. Because of the small difference between the temperature required for denaturing malignant cells and the temperature injurious to healthy cells, a known heating pattern and predictable temperature control is important so that heating is confined to the tissue to be treated. For instance, hyperthermia treatment at the threshold temperature of about 41.5° C. generally has little effect on most malignant growth of cells. However, at slightly elevated temperatures above the approximate range of 43° C. to 45° C., thermal damage to most types of normal cells is routinely observed. Accordingly, great care must be taken not to exceed these temperatures in healthy tissue.

In the case of tissue ablation, a high radio frequency electrical current in the range of about 500 mHz to about 10 gHz is applied to a targeted tissue site to create an ablation volume, which may have a particular size and shape. Ablation volume is correlated to antenna design, antenna performance, antenna impedance, and tissue impedance. The particular type of tissue ablation procedure may dictate a particular ablation volume in order to achieve a desired surgical outcome. By way of example, and without limitation, a spinal ablation procedure may call for a longer, narrower ablation volume, whereas in a prostate ablation procedure, a more spherical ablation volume may be required.

Microwave ablation devices utilize sensors to determine if the system is working properly. However, without delivery of microwave energy, the sensors may indicate that the probe assembly status is normal. Further, defects in antenna assemblies may not be apparent except at high powers. As such, when microwave ablation system is tested using a low power routine a post manufacture defect may not be apparent. This is especially important for high power microwave ablation devices, where failures may result in extremely high temperatures.

Fluid cooled or dielectrically buffered microwave ablation devices may also be used in ablation procedures to cool the microwave ablation probe. Cooling the ablation probe may enhance the overall ablation pattern of antenna, prevent damage to the antenna and prevent harm to the clinician or patient. However, during operation of the microwave ablation device, if the flow of coolant or buffering fluid is interrupted, the microwave ablation device may exhibit rapid failures due to the heat generated from the increased reflected power.

SUMMARY

According to an embodiment of the present disclosure, a microwave ablation system includes an antenna assembly configured to deliver microwave energy from a power source to tissue and a coolant source operably coupled to the power source and configured to selectively provide fluid to the antenna assembly via a fluid path. The system also includes a controller operably coupled to the power source and a sensor operably coupled to the fluid path and the controller. The sensor is configured to detect fluid flow through the fluid path and the controller is configured to control the energy source based on the detected fluid flow.

According to another embodiment of the present disclosure, a microwave ablation system includes an antenna assembly configured to deliver microwave energy from a power source to tissue and a coolant source operably coupled to the power source and configured to selectively provide fluid to the antenna assembly via a fluid path. The system also includes a controller operably coupled to the power source and a capacitive device operably coupled to the fluid path and the controller. The capacitive device is configured to detect fluid flow through the fluid path based on a capacitance of the capacitive device. The controller is configured to control the energy source based on the detected fluid flow.

According to another embodiment of the present disclosure, a method of detecting fluid flow through a microwave ablation system includes the steps of delivering microwave energy from a power source to tissue via an antenna assembly and supplying fluid from a coolant source to the antenna assembly via a fluid path. The method also includes the steps of detecting a capacitance of a capacitive device operably coupled to the fluid path and comparing the detected capacitance to a predetermined range. The method also includes the step of modifying output of energy from the energy source based on the comparison between the detected capacitance and the predetermined range.

According to another embodiment of the present disclosure, a microwave ablation system includes an antenna assembly configured to deliver microwave energy from a power source to tissue and a coolant source operably coupled to the power source and configured to selectively provide fluid to the antenna assembly via a fluid path. The system also includes a controller operably coupled to the power source and a sensor disposed within the fluid path and operably coupled to the controller. The sensor is configured to detect fluid flow through the fluid path. The controller is configured to control the generator based on the detected fluid flow.

According to another embodiment of the present disclosure, a microwave ablation system includes an antenna assembly configured to deliver microwave energy from a power source to tissue and a coolant source operably coupled to the power source and configured to selectively provide fluid to the antenna assembly via a fluid path. The system also includes a controller operably coupled to the power source and an electro-mechanical switch disposed within the fluid path and operably coupled to the controller. The electro-mechanical switch is configured to detect fluid flow through the fluid path based on movement of the switch between an open position and a closed position. The controller is configured to control the generator based on the detected fluid flow.

According to another embodiment of the present disclosure, a method of detecting fluid flow through a microwave ablation system includes the steps of delivering microwave energy from a power source to tissue via an antenna assembly and supplying fluid from a coolant source to the antenna assembly via a fluid path. The method also includes detecting a position of an electro-mechanical switch disposed within the fluid path and modifying output of energy from the energy source based on the detected position.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Figure 1:
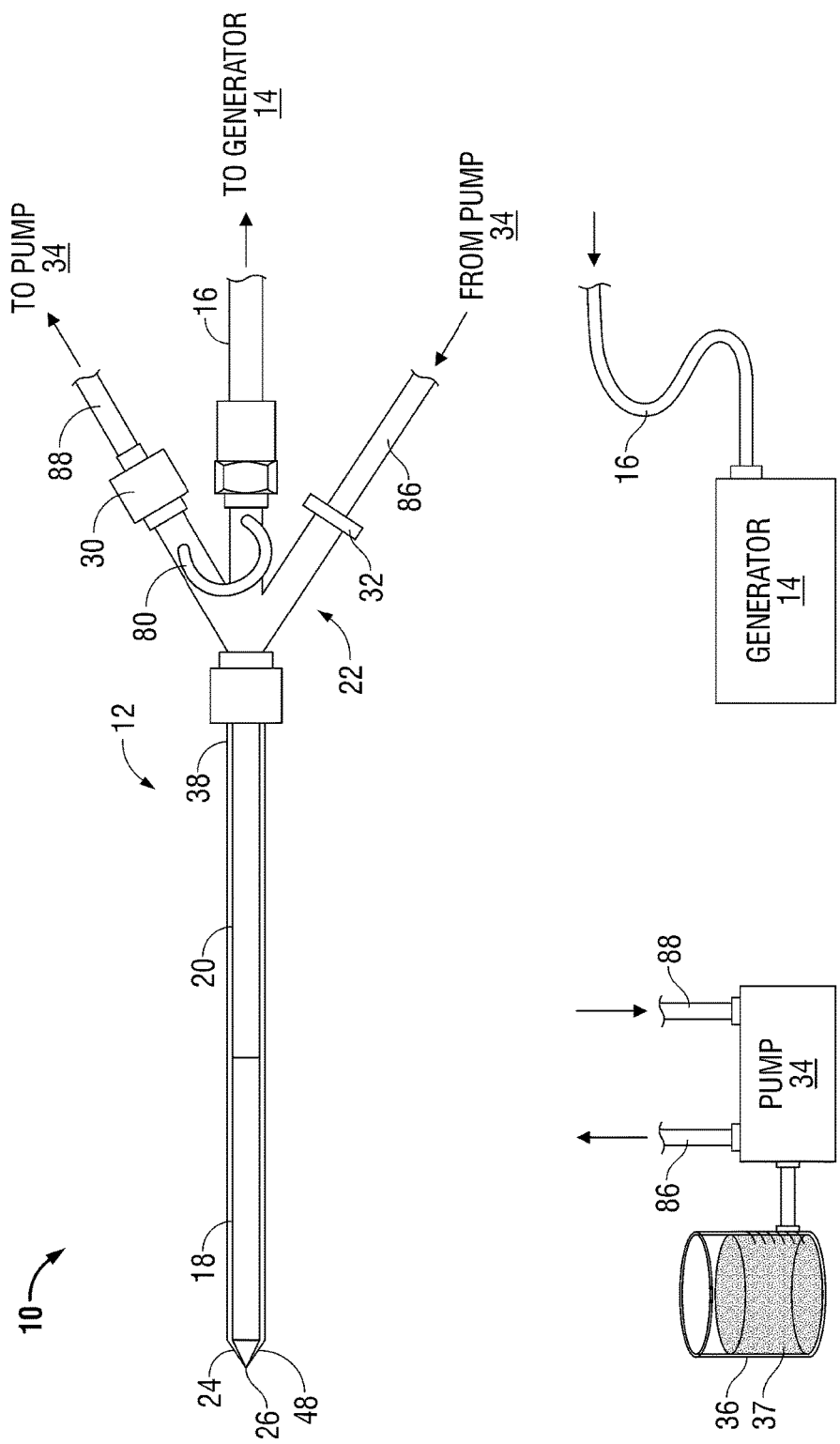
FIG. 1 shows a diagram of a microwave antenna assembly in accordance with an embodiment of the present disclosure.

Embodiments of the presently disclosed apparatus are described in detail below with reference to the drawings wherein like reference numerals identify similar or identical elements in each of the several views. In the discussion that follows, the term "proximal" will refer to the portion of a structure that is closer to a user, while the term "distal" will refer to the portion of the structure that is farther from the user.

Generally, the present disclosure is directed to a microwave antenna assembly having an energy source or generator adapted to deliver energy to tissue via the antenna assembly and a coolant source for circulating a dielectric coolant fluid through the microwave antenna assembly. More particularly, the present disclosure is directed to monitoring fluid flow through the microwave antenna assembly and controlling the energy source output based on the monitored fluid flow to prevent damage to the antenna and/or harm to the clinician or patient caused by overheating of the antenna assembly.

FIG. 1 shows a microwave ablation system 10 that includes a microwave antenna assembly 12 coupled to a microwave generator 14 via a flexible coaxial cable 16. The generator 14 is configured to provide microwave energy at an operational frequency from about 500 MHz to about 5000 MHz, although other suitable frequencies are also contemplated.

In the illustrated embodiment, the antenna assembly 12 includes a radiating portion 18 connected by feedline 20 (or shaft) to the cable 16. More specifically, the antenna assembly 12 is coupled to the cable 16 through a connection hub 22 having an outlet fluid port 30 and an inlet fluid port 32 that are connected in fluid communication with a sheath 38. The sheath 38 encloses radiating portion 18 and feedline 20 to form a chamber 89 (FIG. 2) allowing a coolant fluid 37 to circulate from ports 30 and 32 around the antenna assembly 12. The ports 30 and 32 are also coupled to a supply pump 34 that is, in turn, coupled to a supply tank 36 via supply line 86. The supply pump 34 may be a peristaltic pump or any other suitable type. The supply tank 36 stores the coolant fluid 37 and, in one embodiment, may maintain the fluid at a predetermined temperature. More specifically, the supply tank 36 may include a coolant unit that cools the returning liquid from the antenna assembly 12. In another embodiment, the coolant fluid 37 may be a gas and/or a mixture of fluid and gas.

Figure 2:
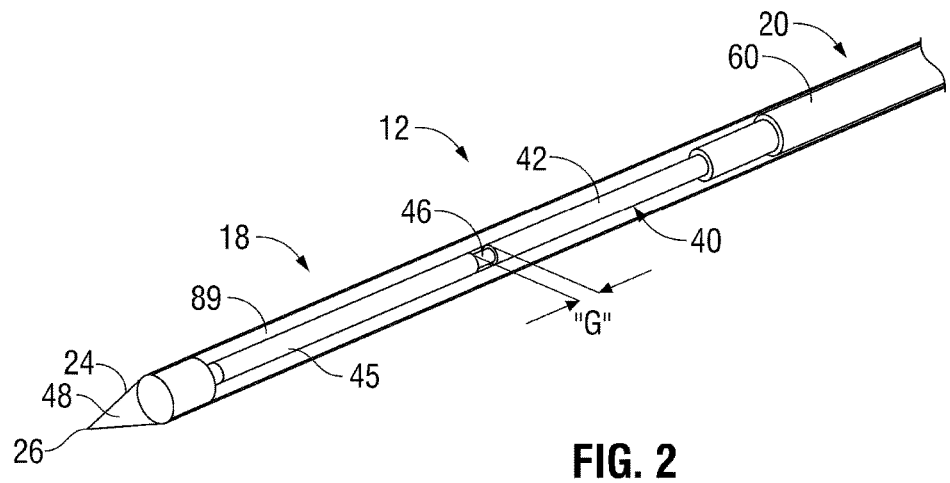
FIG. 2 shows a perspective view of a distal end of the microwave antenna assembly of FIG. 1.

FIG. 2 illustrates the radiating portion 18 of the antenna assembly 12 having a dipole antenna 40. The dipole antenna 40 is coupled to the feedline 20 that electrically connects antenna assembly 12 to the generator 14. The dipole antenna 40 includes a proximal portion 42 and a distal portion 44 interconnected at a feed point 46. The distal portion 44 and the proximal portion 42 may be either balanced (e.g., of equal lengths) or unbalanced (e.g., of unequal lengths). A dipole feed gap "G" is disposed between the proximal and distal portions 42 and 44 at the feed point 46. The gap "G" may be from about 1 mm to about 3 mm. In one embodiment, the gap "G" may be thereafter filled with a dielectric material at the feed point 46. The dielectric material may be polytetrafluoroethylene (PTFE), such as Teflon® sold by DuPont of Willmington, Del. In another embodiment, the gap "G" may be coated with a dielectric seal coating.

With reference to FIG. 2, the antenna assembly 12 also includes a choke 60 disposed around the feedline 20. The choke 60 may be a quarter-wavelength shorted choke that is shorted to the feedline 20 at the proximal end (not illustrated) of the choke 60 by soldering or other suitable methods.

Assembly 12 also includes a tip 48 having a tapered end 24 that terminates, in one embodiment, at a pointed end 26 to allow for insertion into tissue with minimal resistance at a distal end of the radiating portion 18. In those cases where the radiating portion 18 is inserted into a pre-existing opening, tip 48 may be rounded or flat. The tip 48 may be formed from a variety of heat-resistant materials suitable for penetrating tissue, such as metals (e.g., stainless steel) and various thermoplastic materials, such as poletherimide, and polyamide thermoplastic resins.

Figure 3:
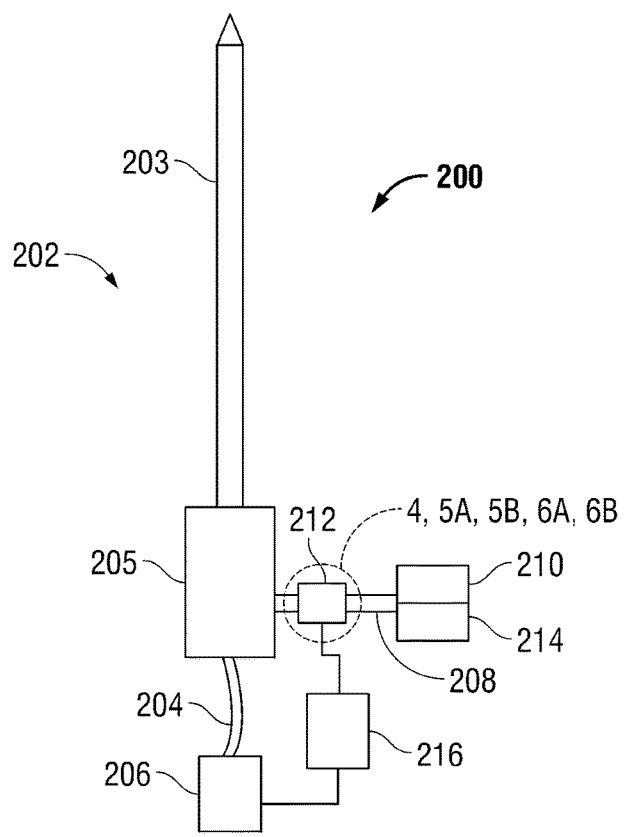
FIG. 3 shows a system block diagram of a microwave antenna assembly according to another embodiment of the present disclosure.

With reference to FIG. 3, a microwave ablation system, shown generally as 200, according to an embodiment of the present disclosure is depicted. The system 200 includes an ablation device 202 having an antenna 203 and a handle 205 used to ablate tissue. A generator 206, which is substantially similar to power generating source 28, supplies the ablation device 202 with energy via coaxial cable 204. Ablation device is supplied with coolant or fluid from coolant supply 210 through conduit 208. The coolant flows through the ablation device 202 as described above and exits the ablation device via conduit 208 into chamber 214. Conduit 208 may be a multi-lumen conduit having an inflow lumen for supplying the ablation device 202 with coolant and an outflow lumen for coolant to exit the ablation device 202 into the chamber 214. Additionally, conduit 208 may be provided as two separate conduits, an inflow conduit and an outflow conduit.

As shown in FIG. 3, a sensor 212 is provided to monitor the flow rate of fluid through conduit 208. As described above, when coolant circulation is interrupted, the ablation device tends to exhibit rapid failures. Further, when coolant circulation is too great and/or the flow rate of fluid through conduit 208 exceeds a predetermined threshold maximum (e.g., 100 ml/min, 130 ml/min, etc.), the ablation device may be exhibiting symptoms of a fluid leak. By monitoring the fluid flow through microwave ablation system 200, damage to the ablation device as well as harm to the clinician or patient may be prevented. Controller 216 is coupled to generator 206 and is configured to control generator 206 based on an input or signal from sensor 212. Controller 216 may be a microprocessor or any logic circuit able to receive an input or signal from sensor 212 and provide an output to control generator 206. Controller 216 may be operably coupled to a storage device or memory (not shown) configured to store programmable instructions, historical data, lookup tables, operating parameters, etc. Sensor 212 may be a single sensor or an array of sensors configured to detect operational parameters of the ablation device 202 in order to determine if the microwave ablation system 200 is functioning properly. In use, sensor 212 provides an electrical signal to the controller 216 that represents a real-time measurement or indication such as fluid flow, pressure, capacitance, etc., as described in further detail below. Controller 216 compares the electrical signal to a predetermined range. If the electrical signal is within a predetermined range, the controller 216 controls the generator 206 to continue with the ablation procedure. If the electrical signal is outside the predetermined range, the controller 216 controls the generator 206 to cease the ablation procedure and/or modify generator 206 output. For example, the predetermined range may be a range of fluid flow rates through conduit 208. In one embodiment, the predetermined range of flow rate requirements is between about 70 ml/min and about 130 ml/min. In this scenario, an operating range of flow rates may be between about 100 ml/min and about 120 ml/min. In another embodiment, the predetermined range of flow rate requirements is between about 40 ml/min and about 100 ml/min. In this scenario, an operating range of flow rates may be between about 60 ml/min and about 80 ml/min.

Sensor 212 may be incorporated into ablation device 202 or controller 216 may be coupled to ablation device 202 and/or controller 216. Sensor 212 may be placed anywhere along the fluid path. For instance, sensor 212 may be placed in antenna 203, handle 205 or along the inflow lumen or outflow lumen of conduit 208. The sampling rate of sensor 212 is sufficient to detect intermittent problems with the flow of fluid through the ablation system 200. The sensor 212 is configured to detect fluid flow during startup before microwave energy is delivered to the ablation device 202 or during an ablation procedure.

Figure 4:
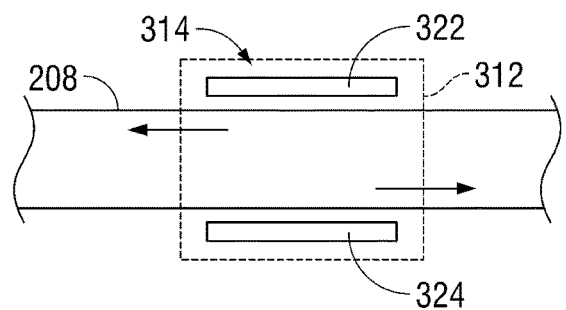
FIG. 4 shows the area of detail of FIG. 3 according to an embodiment of the present disclosure.

With reference to FIG. 4, a sensor 312 according to another embodiment of the present disclosure is shown operably coupled to conduit 208. Sensor 312 is configured to operate in conjunction with microwave ablation system 200 as substantially described above with reference to sensor 212. Sensor 312 is a parallel plate capacitor 314 including capacitive plates 322 and 324 disposed about conduit 208. More specifically, conduit 208 and its contents (e.g., fluid, air, air bubbles, etc.) are disposed between capacitive plates 322 and 324 to operate as a dielectric of capacitor 314. Capacitive plates 322 and 324 may be disposed about the inflow lumen of conduit 208, the outflow lumen of conduit 208, or both the inflow and outflow lumens of conduit 208. Capacitance of capacitor 314 is calculated using the following formula (1):

$$C = \varepsilon * A/d \qquad (1)$$

Applying equation (1) to the embodiment illustrated in FIG. 4, C is the capacitance of capacitor 314, A is the area of capacitive plates 322 and 324, d is the distance between capacitive plates 322 and 324, and ∈ is the permittivity of the dielectric between capacitive plates 322 and 324 (e.g., conduit 208 and its contents). Given a constant area A of capacitive plates 322, 324 and a constant distance d between capacitive plates 322, 324, any change in permittivity ε of the dielectric between capacitive plates 322, 324, namely conduit 208 and its contents, causes a change in conductivity of capacitor 314. For example, if fluid flow through conduit 208 is interrupted resulting in the presence of air, air bubbles, and/or a lack of fluid flow through a portion of conduit 208 disposed between capacitive plates 322, 324, the ability of conduit 208 and its contents to transmit an electric field decreases, i.e., the permittivity ∈ of conduit 208 and its contents decreases, resulting in a decrease in conductivity C of capacitor 314. That is, the presence of air within conduit 208, rather than fluid, effectively decreases the permittivity ∈ of the dielectric between capacitive plates 322, 324 since the dielectric constant (or permittivity) of the fluid (e.g., water) is significantly higher than air.

Sensor 312 provides an electrical signal to the controller 216 indicating the capacitance C of capacitor 314 and/or the change in capacitance C of capacitor 314. Controller 216 compares the electrical signal to a predetermined range. If the electrical signal is within the predetermined range, the controller 216 controls the generator 206 to continue with the ablation procedure. If the electrical signal is outside the predetermined range, the controller 216 controls the generator to terminate the ablation procedure and/or modify generator 206 output.

In another embodiment, sensor 312 may be disposed about the outflow lumen of conduit 208 to detect changes in capacitance C of capacitor 314 due to steam caused by overheating of ablation device 202. In this scenario, the presence of steam in conduit 208 changes the permittivity ε of the dielectric between capacitive plates 322, 324, thereby changing the capacitance C of capacitor 314.

Figure 5A:
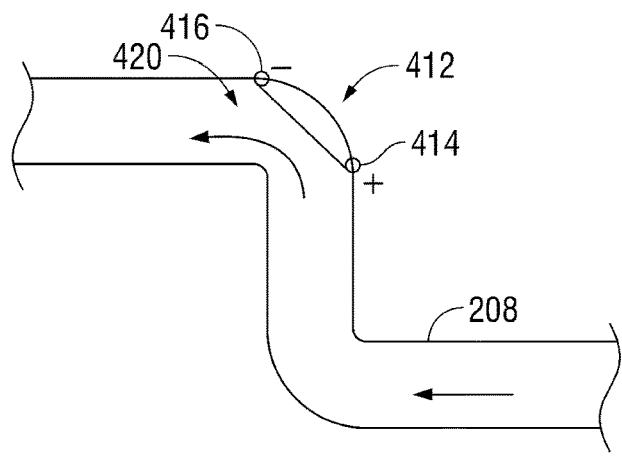
FIGS. 5A and 5B show the area of detail of FIG. 3 according to another embodiment of the present disclosure.
Figure 5B:
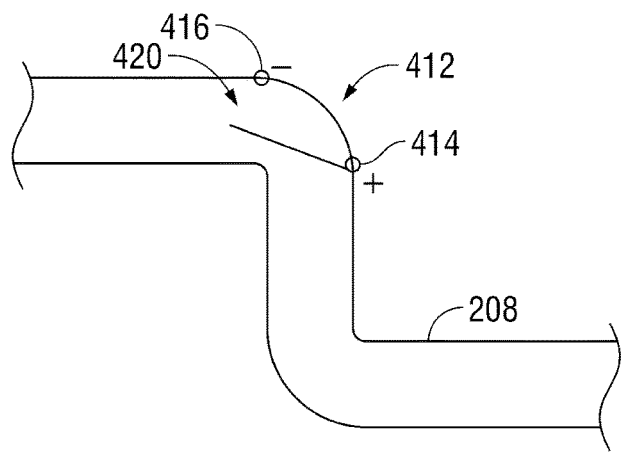

Referring now to FIGS. 5A and 5B, a sensor 412 according to another embodiment of the present disclosure is shown operably coupled to conduit 208. Sensor 412 is configured to operate in conjunction with microwave ablation system 200 as substantially described above with reference to sensor 212. Sensor 412 includes an electromechanical switch 420 disposed in the fluid path through conduit 208. Switch 420 may be disposed within the inflow lumen of conduit 208, within the outflow lumen of conduit 208, or within both the inflow and outflow lumens of conduit 208. Switch 420 operates to open or close an electrical circuit electrically connected to controller 216 depending on fluid flow through conduit 208. More specifically, switch 420 is hinged at one end to a pivot 414 disposed on an inner surface of conduit 208 and is configured at an opposing end to movably engage a contact 416 disposed on an opposing inner surface of conduit 208 upon pivotal movement about pivot 414 to close an electrical circuit between sensor 412 and controller 216. In the illustrated embodiment, switch 420 is naturally biased in the open position by pivot 414.

As best shown in FIG. 5A, sufficient fluid flow through conduit 208 (e.g., 70 ml/min≤fluid flow rate≤130 ml/min), as depicted by directional arrows illustrated within conduit 208, biases switch 420 to the closed position, thereby closing the electrical circuit between sensor 412 and controller 216. The closed electrical circuit indicates to the controller 216 that sufficient fluid flow exists through conduit 208. As best shown in FIG. 5B, insufficient fluid flow through conduit 208 allows switch 420 to return to its naturally biased open position, thereby opening the electrical circuit between sensor 412 and controller 216. The open electrical circuit indicates to the controller 216 that insufficient fluid flow (e.g., fluid flow rate <70 ml/min) exists through conduit 208. As such, if switch 420 is in the closed position, i.e., contact 416 is engaged by switch 420, the controller 216 controls the generator 206 to continue with the ablation procedure. If switch 420 is in the open position, i.e., switch 420 is disengaged from contact 416, the controller 216 controls the generator to terminate the ablation procedure and/or modify generator 206 output. Sufficient fluid flow and/or insufficient fluid flow may be dictated by a predetermined range of flow rate requirements depending on the ablation device 202 used.

Figure 6A:
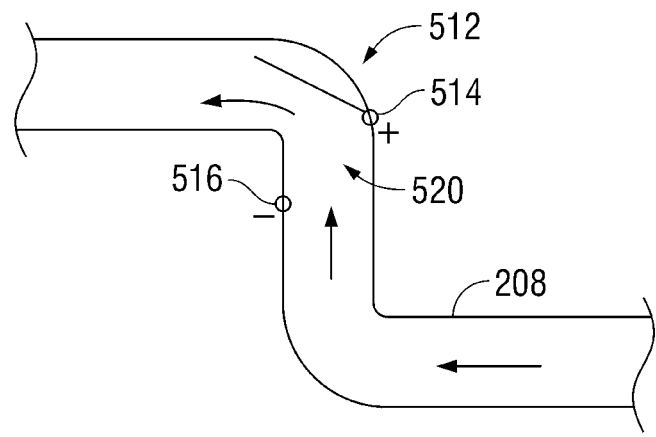
FIGS. 6A and 6B show the area of detail of FIG. 3 according to yet another embodiment of the present disclosure.
Figure 6B:
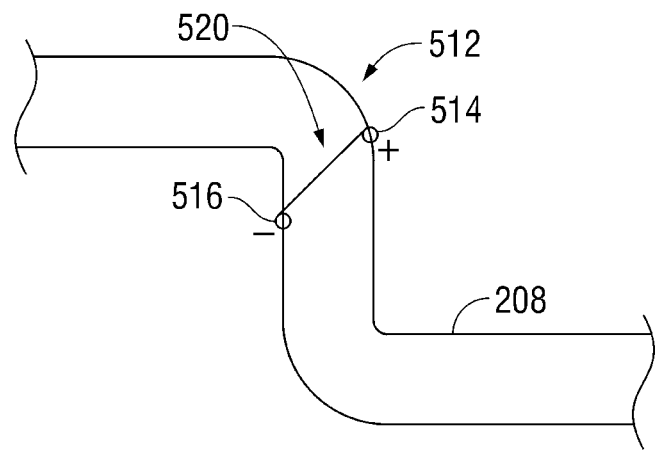

Referring now to FIGS. 6A and 6B, a sensor 512 according to another embodiment of the present disclosure is shown operably coupled to conduit 208. Sensor 512 is configured to operate in conjunction with microwave ablation system 200 as substantially described above with reference to sensor 212. Sensor 512 includes an electromechanical switch 520 disposed in the fluid path through conduit 208. Switch 520 may be disposed within the inflow lumen of conduit 208, within the outflow lumen of conduit 208, or within both the inflow and outflow lumens of conduit 208. Switch 520 operates to open or close an electrical circuit electrically connected between sensor 512 and controller 216 depending on fluid flow through conduit 208. More specifically, switch 520 is hinged at one end to a pivot 514 disposed on an inner surface of conduit 208 and is configured at an opposing end to movably engage a contact 516 disposed on an opposing inner surface of conduit 208 upon pivotal movement about pivot 514 to close an electrical circuit between sensor 512 and controller 216. In the illustrated embodiment, switch 520 is naturally biased in the closed position by pivot 514.

As best shown in FIG. 6A, sufficient fluid flow through conduit 208 (e.g., 40 ml/min≤fluid flow rate≤100 ml/min), as indicated by directional arrows through conduit 208, biases switch 520 to the open position, thereby opening the electrical circuit between sensor 512 and controller 216. The open electrical circuit indicates to the controller 216 that sufficient fluid flow exists through conduit 208. As best shown in FIG. 6B, insufficient fluid flow through conduit 208 allows switch 520 to return to its naturally biased closed position, thereby closing the electrical circuit between sensor 512 and controller 216. The closed electrical circuit indicates to the controller 216 that insufficient fluid flow exists (e.g., fluid flow rate <40 ml/min) through conduit 208. As such, if switch 520 is in the open position, i.e., switch 520 is disengaged from contact 516, the controller 216 controls the generator 206 to continue with the ablation procedure. If switch 520 is in the closed position, i.e., contact 516 is engaged by switch 520, the controller 216 controls the generator to terminate the ablation procedure and/or modify generator 206 output.

Referring to the illustrated embodiments of FIGS. 5A, 5B, 6A, and 6B, the circuitry connecting sensor 412 and/or 512 to the controller 216 for purposes of switch state detection may include a resistor (not shown) in series with switch 420, 520. In this scenario, the total series resistance of the switch 420, 520 and in-line resistor may be monitored by the controller 216 to control generator 206 output.

Figure 7:
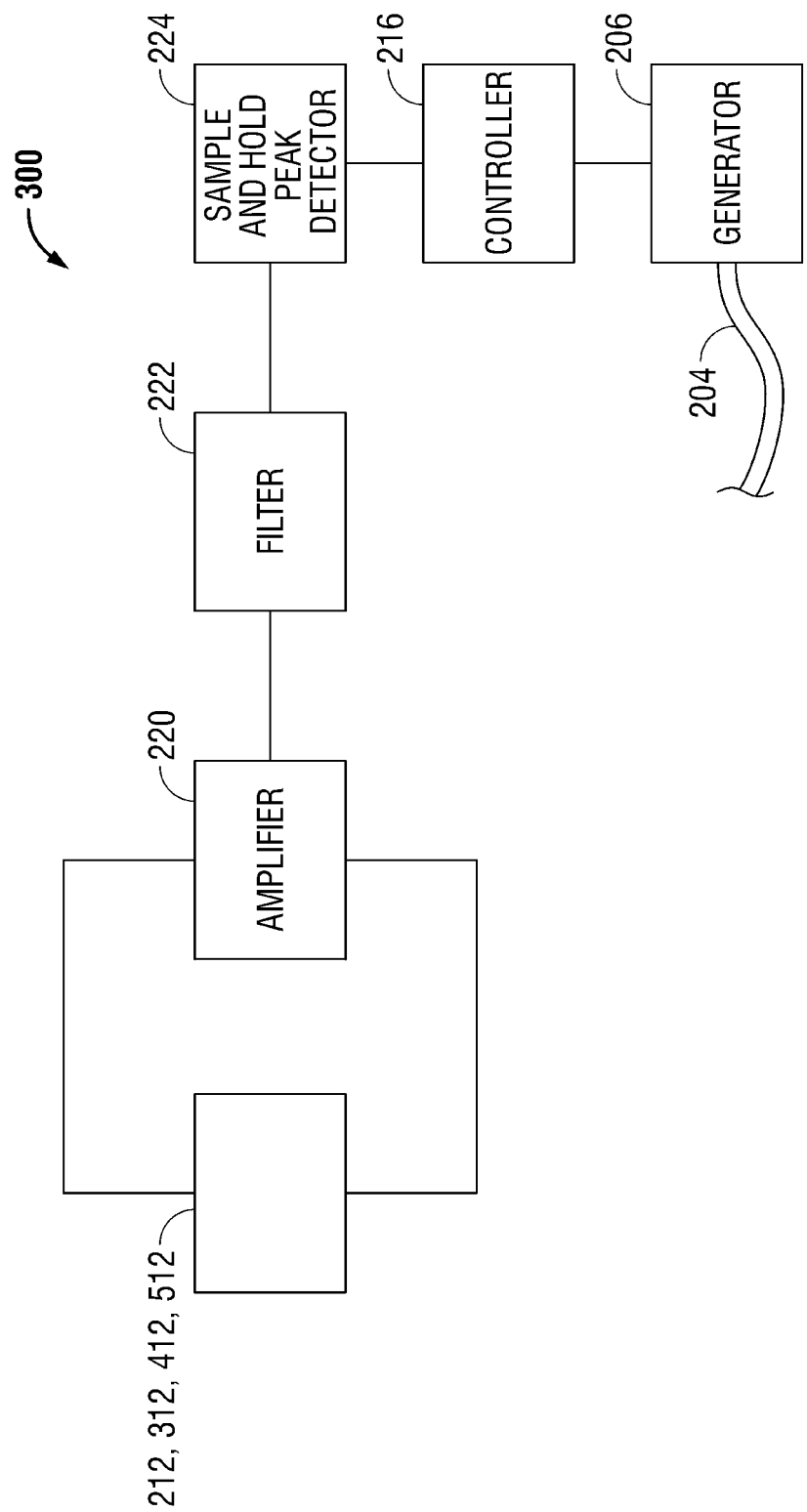
FIG. 7 shows a system block diagram of a signal processing circuit according to an embodiment of the present disclosure.

With reference to FIG. 7, a signal processing circuit 300 may be incorporated within microwave ablation system 200 and electrically connected between sensor 212, 312, 412, 512 and controller 216. Circuit 300 processes electrical signals sent from sensor 212, 312, 412, 512 to controller 216 for the purpose of controlling generator 206 output, as described above with respect to FIGS. 4, 5A, 5B, 6A, and 6D.

More specifically, circuit 300 includes an amplifier 220 incorporating the sensor 212, 312, 412, 512 in a resonant feedback loop. Amplifier 220 may be, for example, a Hartley Oscillator including a tuning capacitor in parallel with two inductors in series. In embodiments incorporating sensor 312, capacitor 314 may operate as the tuning capacitor. In embodiments incorporating sensors 212, 412, or 512, a tuning capacitor electrically connected in series with sensor 212, 412, 512 may be added to amplifier 220.

The output of amplifier 220 is fed into a band pass filter 222 centered on the resonant frequency consistent with fluid flow through conduit 208. That is, in the embodiment of FIG. 4, filter 222 is centered on the resonant frequency consistent with fluid flow within conduit 208 between capacitive plates 322, 324. In the embodiments of FIGS. 5A, 5B, 6A, and 6B, filter 222 is centered on the resonant frequency consistent with fluid flow through switch 420 (FIGS. 5A and 5B) or switch 520 (FIGS. 6A and 6B).

A sample-and-hold peak detector circuit 224 is operably coupled to the filter 222 output such that filter 222 output is sampled and held steady by circuit 224. Circuit 224 samples filter 222 output at a rate sufficient to detect intermittent interruptions of fluid flow through conduit 208 and/or the presence of small air bubbles in conduit 208. In the embodiment of FIG. 4, absence of a peak in the filter 222 output as detected by circuit 224 indicates air (or air bubbles) passing through conduit 208 at capacitive plates 322, 324, as described above with respect to FIG. 4. In the embodiments of FIGS. 5A, 5B, 6A, and 6D, a peak in the filter 222 output as detected by circuit 224 indicates the position of switch 420 (FIGS. 5A and 5B) or switch 520 (FIGS. 6A and 6B) and/or fluid flow through conduit 208 as being sufficient or insufficient, as described above with respect to FIGS. 5A, 5B, 6A, and 6D.

The described embodiments of the present disclosure are intended to be illustrative rather than restrictive, and are not intended to represent every embodiment of the present disclosure. Various modifications and variations can be made without departing from the spirit or scope of the disclosure as set forth in the following claims both literally and in equivalents recognized in law.

What is claimed is:

1. A microwave ablation system comprising:
   a power source configured to generate microwave energy;
   an antenna assembly coupled to the power source;
   a coolant source coupled to the antenna assembly and configured to supply a fluid through a fluid path to the antenna assembly;
   a sensor coupled to the fluid path and configured to generate an electrical signal indicative of a flow of the fluid through the fluid path;
   a signal processing circuit coupled to the sensor and configured to detect at least one peak of the electrical signal being indicative of an interruption in the flow of the fluid through the fluid path; and
   a controller configured to automatically adjust output of the microwave energy from the power source based on the detected peak.

2. The microwave ablation system according to claim 1, wherein the sensor is an electro-mechanical switch and the electrical signal is generated based on a position of the electro-mechanical switch.

3. The microwave ablation system according to claim 1, wherein the sensor is a capacitive device and the electrical signal is generated based on a capacitance of the capacitive device.

4. The microwave ablation system according to claim 3, wherein the capacitive device comprises a dielectric disposed between a pair of parallel capacitive plates.

5. The microwave ablation system according to claim 4, wherein the capacitance of the capacitive device is based on a permittivity of the dielectric disposed between the capacitive plates.

6. The microwave ablation system according to claim 1, wherein the antenna assembly is coupled to the power source by a feedline and the antenna assembly includes radiating section connected to the feedline.

7. The microwave ablation system according to claim 6, wherein the antenna assembly further includes:
   an inlet fluid port and an output fluid port coupled to the coolant source through the fluid path; and
   a sheath in fluid communication with the inlet fluid port and the output fluid port, the sheath enclosing the radiating section and the feedline and defining a chamber for circulating the fluid.

* * * * *